(12) United States Patent
Ozawa

(10) Patent No.: US 7,884,429 B2
(45) Date of Patent: Feb. 8, 2011

(54) IMPACT SENSOR AND METHOD FOR MANUFACTURING THE IMPACT SENSOR

(75) Inventor: Nobuo Ozawa, Tokyo (JP)

(73) Assignee: Oki Semiconductor Co., Ltd., Tokyo (JP)

( * ) Notice: Subject to any disclaimer, the term of this patent is extended or adjusted under 35 U.S.C. 154(b) by 0 days.

(21) Appl. No.: 12/458,494

(22) Filed: Jul. 14, 2009

(65) Prior Publication Data
US 2010/0015808 A1    Jan. 21, 2010

(30) Foreign Application Priority Data
Jul. 16, 2008    (JP)    ............... 2008-184837

(51) Int. Cl.
*H01L 29/84*    (2006.01)

(52) U.S. Cl. ............ 257/415; 257/414; 257/417; 257/418; 257/419; 257/254; 257/E27.006; 257/E29.167; 438/703; 310/311; 310/328; 310/329

(58) Field of Classification Search ............ None
See application file for complete search history.

(56) References Cited

U.S. PATENT DOCUMENTS 6,327,909 B1 * 12/2001 Hung et al. ............ 73/514.16

2007/0290773 A1 * 12/2007 Bar et al. ............ 333/262

FOREIGN PATENT DOCUMENTS

| JP | 10-068742 A | 3/1998 |
|----|-------------|--------|
| JP | 2002-048814 A | 2/2002 |

* cited by examiner

*Primary Examiner*—Sue Purvis
*Assistant Examiner*—Fei Fei Yeung Lopez
(74) *Attorney, Agent, or Firm*—Rabin & Berdo, P.C.

(57) ABSTRACT

An impact sensor comprises a silicon substrate; an insulating layer formed over the silicon substrate; a plurality of beams having flexibility that are formed of conductive silicon material; a fixing portion to fix a fixed end of each of the beams, the fixing portion being formed of conductive silicon material; a fixed end line at whose one end is formed the fixing portion, the fixed end line being formed of conductive silicon material on the insulating layer; and a free end line having a pressing portion that faces a free end of each of the beams via a space, the free end line being formed of conductive silicon material on the insulating layer. Respective beam widths, each measured in a direction orthogonal to a length direction joining the fixed end and the free end, of the plurality of beams are set different from each other, thus reducing the space occupied by the sensor.

9 Claims, 4 Drawing Sheets

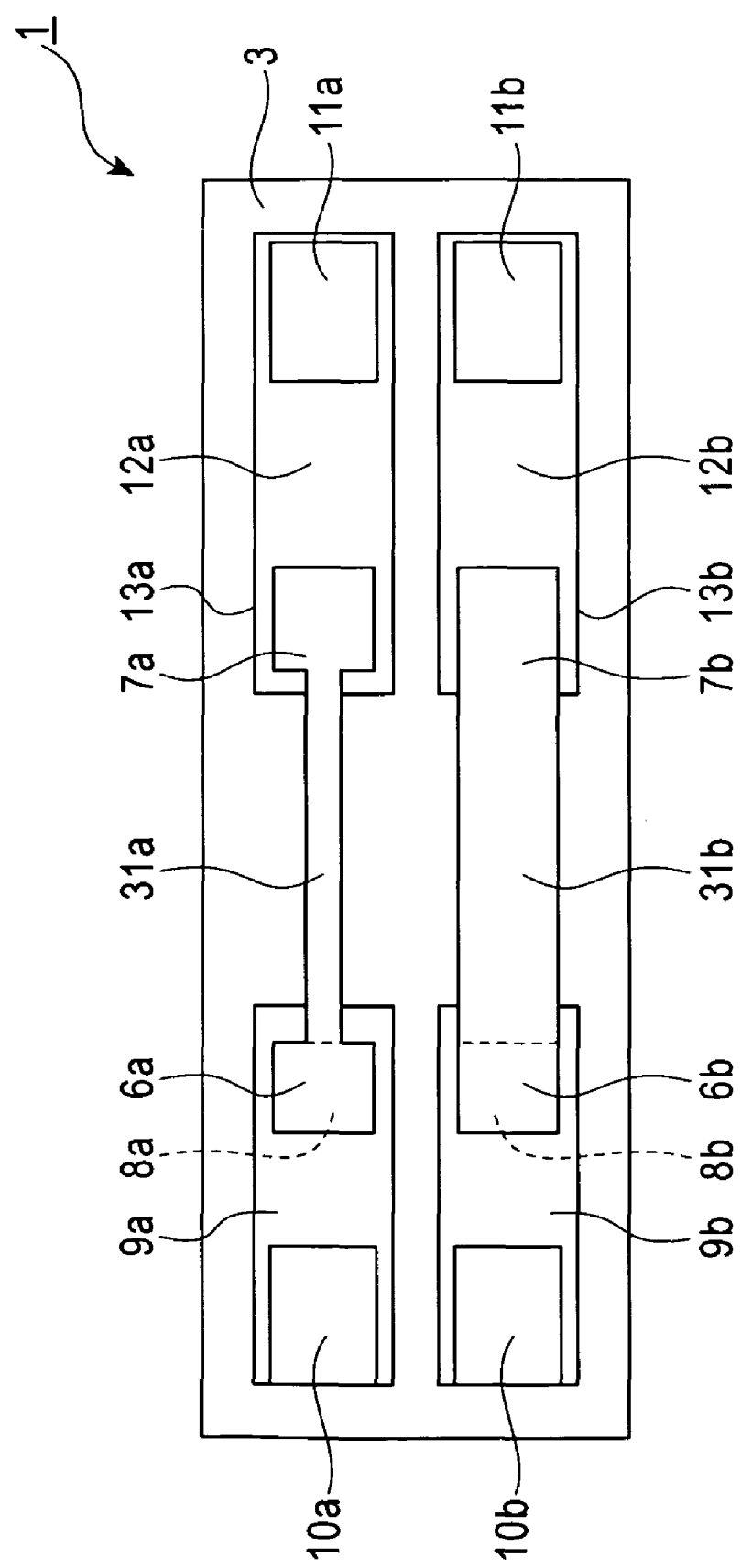

IMPACT SENSOR AND METHOD FOR MANUFACTURING THE IMPACT SENSOR

BACKGROUND OF THE INVENTION

1. Field of the Invention

The present invention relates to an impact sensor which detects that each of accelerations of set acceleration thresholds in magnitude has just acted and a method for manufacturing the impact sensor.

2. Description of the Related Art

In a conventional impact sensor, a first substrate where is formed a cantilever beam having a flexible portion whose one end is fixed to a frame-like support and at whose free end a mass portion is formed, a second substrate on which is formed a first electrode facing a second electrode formed on the mass portion, and a third substrate on which is formed a fourth electrode facing a third electrode formed on the mass portion are laid one over another via a glass layer to form a unit, and the length, width, and thickness of the flexible portion are changed to adjust sensitivity in acceleration detection. A plurality of the units are arranged to detect a plurality of acceleration thresholds. Refer to Japanese Patent Application Laid-Open Publication No. H10-68742 (Reference 1).

There is another device where an annular magnet movably supported by a coil spring and a pair of reed switches having respective contacts located at different positions along the movement direction of the annular magnet are arranged inside a cylindrical tube to form an impact sensor. One or both of the reed switches become closed depending on the position of the magnetic field associated with the annular magnet that moves against the biasing force of the coil spring due to acceleration that varies in magnitude, and thereby different acceleration thresholds are detected. Refer to Japanese Patent Application Laid-Open Publication No. 2002-48814 (Reference 2).

SUMMARY OF THE INVENTION

Due to the recent years of diversification of the distribution system, various commodities have come to be transported. Since transported commodities are subject to various impacts during loading, unloading, transport, and the like, trouble such as a failure or damage may occur in the transported commodities due to the impacts.

If the history of impacts that transported commodities have experienced is recorded, when trouble has occurred in a commodity, the scope of investigation seeking its cause can be narrowed. Hence, it is desired that a small impact recording package or the like having an impact sensor mounted therein which is attachable to carrier boxes be developed.

However, in the technology of Reference 1 cited above, because the impact sensor is structured to have the cantilever beam formed inward of the frame-like support, the area where to form the support is needed, resulting in an increase in the space that the impact sensor occupies. Thus, there is the problem that the impact recording package or the like having the impact sensor mounted therein is enlarged.

Further, in the technology of Reference 2, because the impact sensor is configured to have the annular magnet, etc., arranged inside the cylindrical tube, the entire impact sensor is enlarged. Thus, there is the same problem as above that the impact recording package having the impact sensor mounted therein is enlarged.

If impact recording packages having an impact sensor mounted therein are enlarged and if they are attached to commodities to be transported or the insides of their carrier boxes, the number of the commodities that can be contained in the carrier box is reduced, and if they are attached to the outsides of the carrier boxes, the number of the carrier boxes loaded on a transport machine such as a truck is reduced.

The present invention was made to solve the above problem, and an object thereof is to provide means for reducing the space that an impact sensor occupies.

In order to solve the above problem, an impact sensor of the present invention comprises a silicon substrate; an insulating layer formed over the silicon substrate; a plurality of beams having flexibility that are formed of conductive silicon material; a fixing portion to fix a fixed end of each of the beams, the fixing portion being formed of conductive silicon material; a fixed end line at whose one end is formed the fixing portion, the fixed end line being formed of conductive silicon material on the insulating layer; and a free end line having a pressing portion that faces a free end of each of the beams via a space, the free end line being formed of conductive silicon material on the insulating layer. Respective beam widths, each measured in a direction orthogonal to a length direction joining the fixed end and the free end, of the plurality of beams are set different from each other.

By this means, the present invention produces the following effects. The setting of acceleration thresholds can be easily changed by changing the beam widths. Also, the impact sensor which detects distinguishably that acceleration of one of the two different acceleration thresholds or greater has just acted can be formed with a simple configuration, and in addition the structure for fixing the fixed end of the beam is simplified. Hence the space occupied by the impact sensor can be reduced.

BRIEF DESCRIPTION OF THE DRAWINGS

FIG. 4 is an illustrative view showing a top plan of an impact sensor of Embodiment 2.

DETAILED DESCRIPTION OF THE PREFERRED EMBODIMENTS

Embodiments of an impact sensor and a method for manufacturing the impact sensor according to the present invention will be described below with reference to the accompanying drawings.

Embodiment 1

Figure 1:
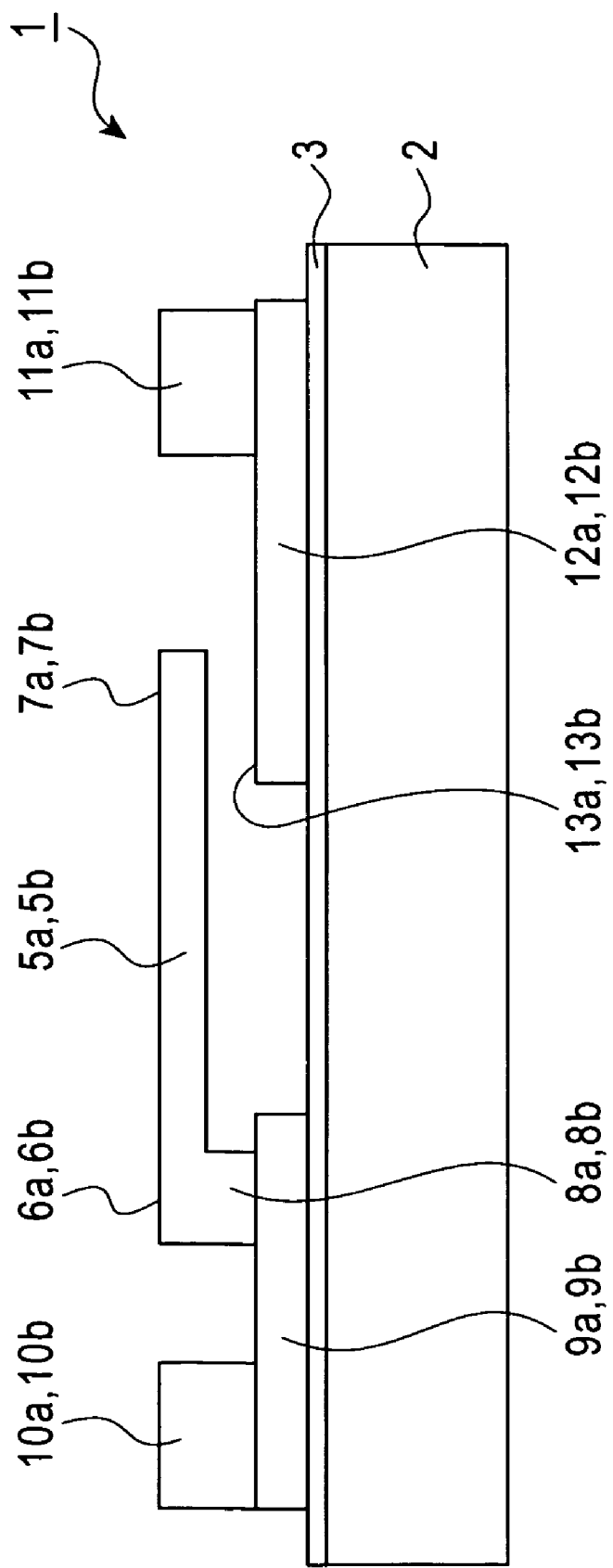
FIG. 1 is an illustrative view showing a side elevation of an impact sensor of Embodiment 1.
Figure 2:
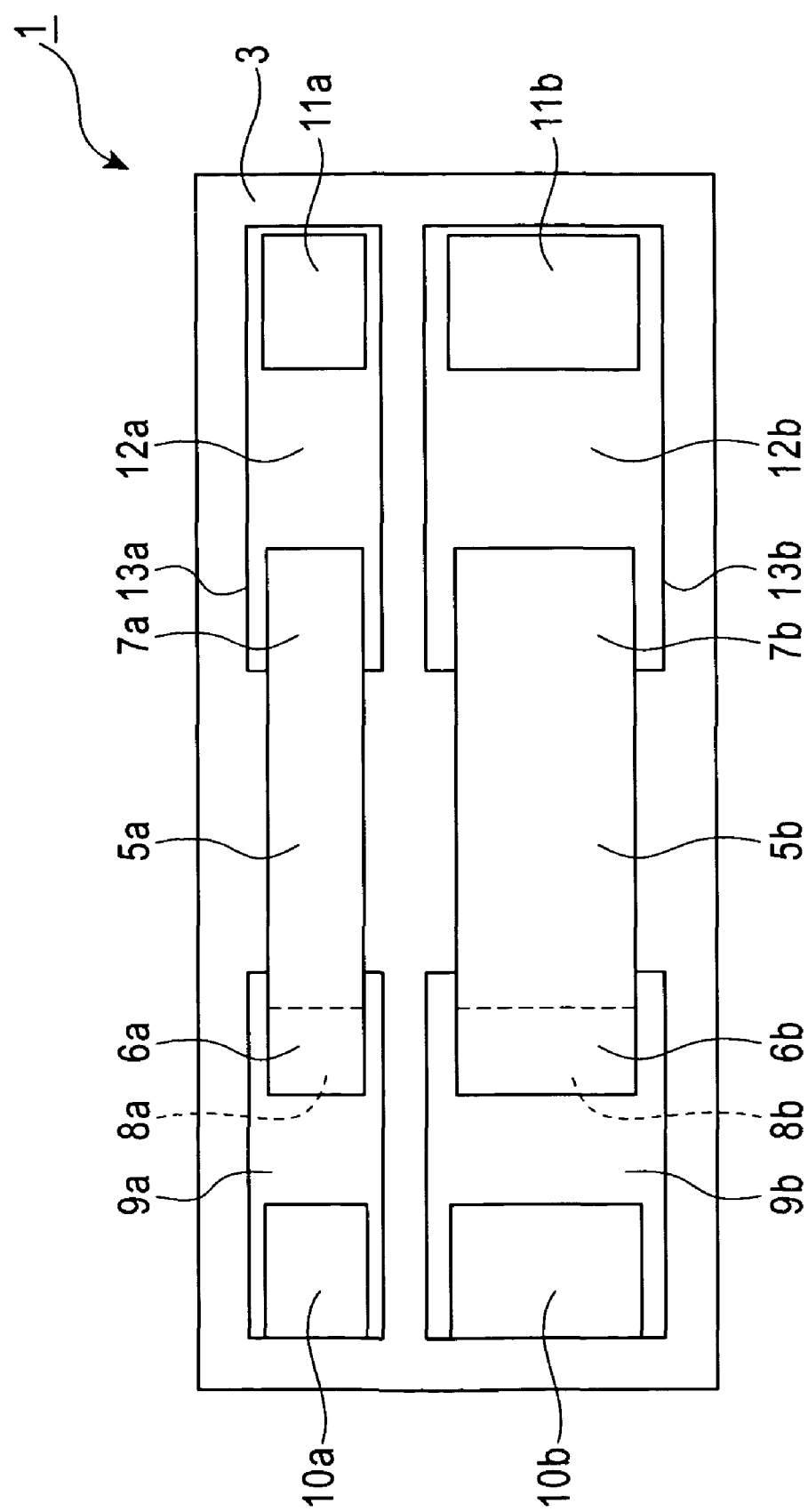
FIG. 2 is an illustrative view showing a top plan of the impact sensor of Embodiment 1.
Figure 3:
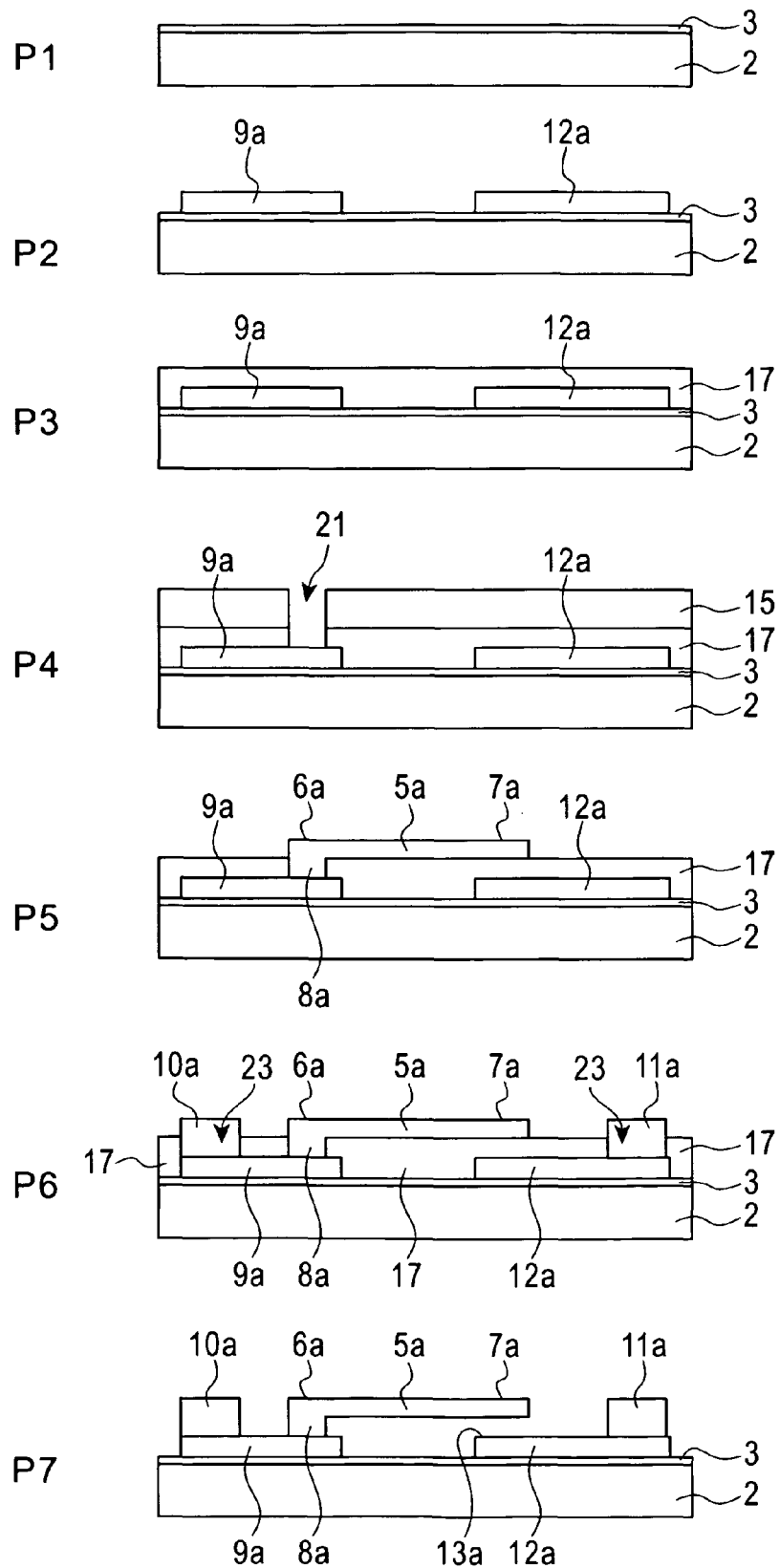
FIG. 3 is an illustrative view showing a method for manufacturing the impact sensor of Embodiment 1.

FIG. 1 is an illustrative view showing a side elevation of an impact sensor of Embodiment 1; FIG. 2 is an illustrative view showing a top plan of the impact sensor of Embodiment 1; and FIG. 3 is an illustrative view showing the method for manufacturing the impact sensor of Embodiment 1.

In FIGS. 1, 2, reference numeral 1 indicates the impact sensor. This impact sensor detects that each of accelerations of two acceleration thresholds in magnitude has just acted and is a sensor of a MEMS (Micro-Electro-Mechanical System) manufactured on a silicon nitride film 3 as an insulating layer made of silicon nitride ($Si_3N_4$) formed over a silicon substrate 2 made of silicon (Si) using silicon micromachining.

The impact sensor 1 comprises beams 5a, 5b; fixed ends 6a, 6b; free end 7a, 7b; fixing portions 8a, 8b; fixed end lines 9a, 9b; pads 10a, 10b, 11a, 11b; free end lines 12a, 12b; and pressing portions 13a, 13b.

Each of the beams 5a, 5b is a flexible plate-like member formed by heating a conductive silicon material which is deposited by CVD (Chemical Vapor Deposition) method. The conductive silicon material is a conductive material such as phosphorus-doped poly-silicon including, as a conductivity-type impurity, an N-type impurity (here phosphorus) such as phosphorus (P) or arsenic (As). The beam 5a is formed extending from a fixed end 6a to a free end 7a (a direction joining the fixed end 6a and the free end 7a is called a length direction). The beam 5b is formed extending from a fixed end 6b to a free end 7b (a direction joining the fixed end 6b and the free end 7b is called a length direction). In reality, as shown in FIG. 2, two beams 5a, 5b of the same length and the same thickness (dimension along a direction orthogonal to the length direction in the cross-section shown in FIG. 1) are provided to be parallel to each other in the length direction. Note that the two beams 5a, 5b are different in the width along a direction orthogonal to the length direction (hereinafter called a beam width) as shown in FIG. 2.

Each of the fixing portions 8a, 8b is made of conductive silicon material like the beams 5a, 5b and functions to fix the fixed ends 6a, 6b of the beams 5a, 5b over the beam widths of the beams 5a, 5b so that the cantilever-like beams 5a, 5b are formed.

Each of the fixed end lines 9a, 9b is made of conductive silicon material such as phosphorus-doped poly-silicon and extends in the direction opposite to the beams 5a, 5b along the length direction of the beams 5a, 5b. Each of the fixing portions 8a, 8b is formed on one end of the fixed end line, and the pads 10a, 10b made of conductive material such as aluminum (Al) are formed on the other end.

Each of the free end lines 12a, 12b is made of conductive silicon material like the fixed end lines 9a, 9b and extends in the direction opposite to the beams 5a, 5b along the length direction of the beams 5a, 5b.

The pressing portion 13a facing the free end 7a of the beam 5a via a space is formed on one end of the free end line (the space between the free end 7a and the pressing portion 13a is called a contact space), and the pad 11a made of conductive material like the pad 10a is formed on the other end. The pressing portion 13b facing the free end 7b of the beam 5b via a space is formed on one end of the free end line (the space between the free end 7b and the pressing portion 13b is called a contact space), and the pad 11b made of conductive material like the pad 10b is formed on the other end.

In the present embodiment, in order to detect accelerations of acceleration thresholds respectively set in them, the two beams 5a, 5b are set to be the same in length and thickness so that the beam dimensions from the fixed ends 6a, 6b to the free ends 7a, 7b in the length direction are the same, and the beam 5a is set to be narrow in beam width (here 5 micrometer), and the beam 5b is set to be broad in beam width (here 15 micrometer).

Their contact spaces are set at the same value, 0.5 micrometer.

In the case of setting acceleration thresholds by the beam width, the average level of the acceleration thresholds that the impact sensor 1 detects is determined by the contact space and thickness, and the plus/minus difference from the average level is set by the beam width.

In FIG. 3, a resist mask 15 as a mask member is a mask pattern formed by exposing and developing a positive or negative type resist coated over the top of the silicon substrate 2 by a spin coat method or the like in photolithography and functions as a mask in an etching process in this embodiment.

a sacrifice oxide film 17 is a phosphorus-doped oxide film (PSG) made of phosphorus-doped silicon oxide ($SiO_2$) and is removed after the beams 5a, 5b; the fixing portions 8a, 8b; and the pads 10a, 10b, 11a, 11b are formed.

The method for manufacturing the impact sensor of this embodiment will be described below according to the order of the processes P in FIG. 3. In addition, in FIG. 3, only the beam 5a, the fixed end 6a, the free end 7a, the fixing portion 8a, the fixed end line 9a, the pads 10a, 11a, the free end line 12a and pressing portion 13a are shown. It goes without saying that the beam 5b, the fixed end 6b, the free end 7b, the fixing portion 8b, the fixed end line 9b, the pads 10b, 11b, the free end line 12b and pressing portion 13b are manufactured at same time.

P1: The silicon substrate 2 having an area on which a large number of the impact sensors 1 can be formed is prepared, and the silicon nitride film 3 of 0.3 μm in thickness made of silicon nitride is formed on the silicon substrate 2 by the CVD method.

P2: Phosphorus-doped poly-silicon is deposited to a thickness of 0.5 μm over the silicon nitride film 3 by the CVD method; a resist mask 15 (not shown) covering regions of the fixed end lines 9a, 9b and the free end lines 12a, 12b is formed by photolithography; using this as a mask, the deposited phosphorus-doped poly-silicon is etched by anisotropic etching to form the fixed end lines 9a, 9b and the free end lines 12a, 12b made of phosphorus-doped poly-silicon on the silicon nitride film 3; and the resist mask 15 is removed.

P3: The sacrifice oxide film 17 about 1.5 μm thick made of phosphorus-doped silicon oxide is formed to cover the silicon nitride film 3, the fixed end lines 9a, 9b, and the free end lines 12a, 12b by the CVD method, and the sacrifice oxide film 17 is polished and flattened at the top by a CMP (Chemical Mechanical Polishing) method so that the thickness measured from the top of the fixed end lines 9a, 9b and the free end lines 12a, 12b becomes 0.5 μm, matching the contact space.

P4: A resist mask 15 having an opening through which the region of the fixing portions 8a, 8b of the fixed end lines 9a, 9b is exposed is formed on the flattened sacrifice oxide film 17 by photolithography, and using this as a mask, the sacrifice oxide film 17 is etched by anisotropic etching to form through holes 21 reaching respectively the fixed end lines 9a, 9b.

P5: The resist mask 15 formed in process P4 is removed; conductive silicon material is deposited into the through hole 21 and onto the sacrifice oxide film 17 by the CVD method to form a conductive silicon layer; and the top of the conductive silicon layer is polished by the CMP method so that the thickness measured from the top of the sacrifice oxide film 17 becomes 1 μm, matching the thickness of the beams 5a, 5b.

Next, a resist mask 15 (not shown) covering regions of the two beams 5a, 5b different in beam width (see FIG. 2) is formed on the polished conductive silicon layer by photolithography; and the conductive silicon layer is etched by anisotropic etching to form the beams 5a, 5b extending to and over the pressing portion 13a, 13b of the free end lines 12a, 12b, and the fixing portions 8a, 8b fixing the respective fixed ends 6a, 6b thereof.

Then, after the resist mask 15 is removed, heat treatment at a temperature of 1,000° C. or greater is performed to remove the distortion of the beams 5a, 5b formed by the CVD method and homogenize their constitution to stabilize the flexibility of the beams 5a, 5b.

P6: After the heat treatment, a resist mask 15 (not shown) covering the sacrifice oxide film 17 and the beams 5a, 5b and having openings through which regions of the respective pads 10a, 10b, 11a, 11b of the fixed end lines 9a, 9b and the free end lines 12a, 12b are exposed, is formed by photolithography; using this as a mask, the sacrifice oxide film 17 is etched by anisotropic etching to form through holes 23 respectively reaching the fixed end lines 9a, 9b and the free end lines 12a, 12b; aluminum is deposited into the through holes 23 and onto the resist mask 15 by a sputtering method to form an aluminum film; and thereafter the resist mask 15 is removed by a liftoff method using an exfoliation agent to form the pads 10a, 10b, 11a, 11b made of aluminum.

P7: After the pads 10a, 10b, 11a, 11b are formed, the silicon oxide is selectively removed. By vapor etching using hydrofluoric acid (HF), the sacrifice oxide film 17 is removed with suppressing the etching of aluminum, and then the silicon substrate 2 is divided into chips with a cutting apparatus using a laser beam to form the impact sensor 1 shown in FIGS. 1, 2.

The impact sensor 1 of the present embodiment formed in this way has the beams 5a, 5b different in beam width, which are different in flexibility depending on the size of the beam width whereas they are the same in length and thickness, and hence when acceleration acts in the direction of the thickness of the beams 5a, 5b, the beams 5a, 5b bend according to their flexibility due to the acceleration, and thereby the extremity of the free end 7a (or 7b) moves toward the pressing portion 13a (or 13b) of the free end line 12a (or 12b), that is, in such a direction as to narrow the contact space.

At this time, if acceleration of the set acceleration threshold or greater acts on the beam high in flexibility, that is, low in stiffness, here the beam 5a, the extremity of the free end 7a of the beam 5a is pressed against the pressing portion 13a of the free end line 12a, thus electrically connecting the pads 10a, 11a.

If acceleration of the set acceleration threshold or greater acts on the beam 5b low in flexibility, the extremities of the free ends 7a, 7b of the beams 5a, 5b are pressed against the pressing portions 13a, 13b of the free end lines 12a, 12b respectively, thus electrically connecting their pads 10a (or 10b) and 11a (or 11b).

By this means, it can be detected distinguishably that acceleration of one of the two different acceleration thresholds or greater has just acted, through conduction between the pad 10a (or 10b) and the pad 11a (or 11b).

In the impact sensor 1 of the present embodiment described above, because the beam width is changed to set acceleration thresholds to be detected, the setting of the acceleration thresholds that the impact sensor 1 detects can be easily changed, and hence a request of a customer for a change in acceleration threshold can be deal with immediately.

Further, in the impact sensor 1 of the present embodiment, because the beam width is changed with the length being the same when changing the flexibility, wasteful space in plan view can be eliminated as compared with the case where the length is changed to change the flexibility.

Yet further, because the impact sensor 1 of the present embodiment comprises the beams 5a, 5b; the fixing portions 8a, 8b; the fixed end lines 9a, 9b; and the free end lines 12a, 12b that are made of conductive silicon material, when the extremity of the free end 7a (or 7b) is pressed against the pressing portion 13a (or 13b) of the free end line 12a (or 12b) because of the flexibility of the beam 5a (or 5b), the pads 10a (or 11a), 10b (or 11b) are electrically connected without special electrodes provided on the free ends 7a, 7b, the fixed end lines 9a, 9b and on the free end lines 12a, 12b. Thus, the configuration of the impact sensor 1 can be simplified, and in addition production costs can be reduced.

Further, in the impact sensor 1 of the present embodiment, since the beams 5a, 5b and the fixing portions 8a, 8b are formed by the CVD method, the structure for fixing the fixed ends 6a, 6b can be simplified without the need for a frame-like support for fixing one end of the beams 5a, 5b, and thus the impact sensor can be made smaller. Hence, the space occupied by the impact sensor 1, that is, the mounting area on a substrate can be reduced, thus miniaturizing devices having the impact sensor 1 mounted therein such as an impact recording package.

Still further, in the method for manufacturing of this embodiment, because the fixed end lines 9a, 9b and the free end lines 12a, 12b formed before the heat treatment in process P5 are formed of conductive silicon material, the beams 5a, 5b stable in quality can be formed without concern about a quality change or melting that might otherwise occur in the fixed end lines 9a, 9b or the like due to the heat treatment for removing distortion of and homogenizing the beams 5a, 5b formed by the CVD method.

Yet further, in the method for manufacturing of this embodiment, since the contact space between the free end 7a (or 7b) and the pressing portion 13a (or 13b) opposite is formed by polishing the sacrifice oxide film 17 at the top by the CMP method, the contact space obtained after the removal of the sacrifice oxide film 17 can be formed accurately.

Moreover, in the method for manufacturing of this embodiment, because the silicon nitride film 3 made of silicon nitride different from silicon oxide forming the sacrifice oxide film 17 is used as the insulating layer, when forming each of the beams 5a, 5b like a cantilever beam to form the contact space between the beam 5a (or 5b) and the free end line 12a (or 12b), silicon oxide can be selectively etched with suppressing the etching rates of the silicon nitride film 3 and of the beams 5a, 5b, the free end lines 12a, 12b, and the like that are made of silicon. Hence, the beams 5a, 5b and the contact space can be formed easily and accurately.

Where using the miniaturized impact sensor 1 of the present embodiment as an impact recording package to record the history of impacts experienced, the package may be configured to have the impact sensor together with an LSI comprising a CPU, memory, a timer, and the like mounted on a substrate.

By this means, the mounting area for the impact sensor 1 on the substrate can be reduced, thus miniaturizing the impact recording package, and in addition a small impact recording package can be obtained where the LSI determines that the respective paths between the pads 10a, 10b, 11a, 11b of the two beams 5a, 5b having different beam widths have been made conductive by the action of acceleration of their set acceleration threshold or greater, distinguishing the two acceleration thresholds and recording their history.

Although the present embodiment describes that the sacrifice oxide film 17 is removed by vapor etching using hydrofluoric acid, it may be removed by wet etching using buffered hydrofluoric acid.

Although the present embodiment describes that after the removal of the sacrifice oxide film 17, the silicon substrate 2 having a large number of impact sensors 1 formed thereon is divided into chips, it may be cut before the removal of the sacrifice oxide film 17. By this means, damage to the thin beams 5a, 5b can be prevented when cutting, and in addition debris from cutting can be prevented from entering the contact space or the like, thus improving the quality of the impact sensor 1.

This applies especially to the case of using a cutting apparatus that cuts a silicon substrate into chips with use of a dicing blade rotating at high speed as cutting fluid is jetted.

In this case, the sacrifice oxide film 17 of the divided impact sensors 1 may be removed in a batch by the same vapor etching or wet etching as above.

As describe above, in the present embodiment the impact sensor is provided with the fixed end line and the free end line of conductive silicon material formed on the silicon nitride film over the silicon substrate, and the two flexible plate-like beams of conductive silicon material whose fixed end is fixed to the fixing portion of conductive silicon material formed on the fixed end line and whose free end faces the pressing portion of the free end line via the contact space, and the beam widths of the two beams are set different. Hence, the setting of acceleration thresholds can be easily changed by changing the beam widths. Also, the impact sensor which detects distinguishably that acceleration of one of the two different acceleration thresholds or greater has just acted can be formed with a simple configuration, and in addition the structure for fixing the fixed end of the beam is simplified. Hence the space occupied by the impact sensor can be reduced.

Although the present embodiment describes that two beams different in beam width are provided, the number of beams having different beam widths may be three or greater, not being limited to two. In this case, a small impact sensor which detects distinguishably three or more acceleration thresholds is obtained.

Embodiment 2

FIG. 4 is an illustrative view showing a top plan of an impact sensor of Embodiment 2.

The same reference numerals are used to denote the same or like parts as in Embodiment 1 with description thereof being omitted.

Beams 31a, 31b of the present embodiment are formed such that as shown in FIG. 4, with the beam widths of the fixed ends 6a and 6b being the same, the beam widths of the beams 31a, 31b except the fixed ends 6a, 6b are different. In order to detect accelerations of acceleration thresholds respectively set in them, with the two beams 31a, 31b being the same in length and thickness, the beam width of the beam 31a except the fixed end 6a is set to be narrow (here 3 μm), and the beam width of the beam 31b except the fixed end 6b is set to be the same as that of the fixed end 6a (here 5 μm) like in the beam 5a, 5b of Embodiment 1. Their contact spaces are set at the same value, 0.5 μm.

Although in this embodiment the free end 7a of the beam 31a is set to be the same in beam width as the fixed end 6a to secure a pressing area when pressing against the pressing portion 13a, the beam width of the free end 7a may be set at the narrowed beam width if the pressing area can be secured.

Where acceleration thresholds are set by the beam width of the beam except the fixed ends 6a, 6b, the average level of the acceleration thresholds that the impact sensor 1 detects is determined by the contact space and thickness, and one beam for detecting the maximum acceleration threshold is formed to have the same beam width along the length direction from the fixed end 6b to the free end 7b like the beam 31b, and in the other beam, with its fixed ends 6a having that beam width, a decrease in acceleration threshold is set by its different beam width like in the beam 31a.

This impact sensor 1 is produced in the same way as in the method for manufacturing (see FIG. 3) of Embodiment 1. In this case, in process P5, the resist mask 15 formed on the conductive silicon layer to cover regions where to form the two beams 5a, 5b is formed to cover regions where to form the two beams 31a, 31b shown in FIG. 4.

In the impact sensor 1 having the above-described configuration, with the widths of the fixed ends 6a, 6b of the beams 31a, 31b being the same, the acceleration threshold to be detected is set by changing the beam width of the beam 31a except the fixed end 6a. Hence, without changing the formed position of the beams 31a, 31b, the setting of the acceleration thresholds can be easily changed, and in addition the pads 10a, 10b, 11a, 11b can always be formed at the same positions, so that the mount-ability for devices where to mount the impact sensor 1 is not changed. Thus, the miniaturized impact sensor 1 of this embodiment can be easily incorporated in them, and a request of a customer for a change in acceleration threshold can be deal with immediately, and in addition on the customer side, the impact sensor 1 having the setting of the acceleration thresholds changed can be easily incorporated.

Further, where three or more of the beams are formed, their forming pitches can be set equal. Hence, the mounting area for the impact sensor 1 which detects three or more acceleration thresholds can be reduced, and the impact sensor 1 can be easily incorporated.

As described above, the present embodiment produces the same effect as the embodiment 1, and in addition with the beam widths of the fixed ends of the plurality of beams being the same, by setting the beam widths of the beams except the fixed ends to be different, the setting of the acceleration thresholds can be easily changed without changing the formed positions of the beams, and in addition the pads can always be formed at the same positions, so that the mount-ability for devices where to mount the impact sensor is not changed. Thus, the miniaturized impact sensor can be easily incorporated in them.

Although the above embodiments describe that the conductive silicon material forming the beam, the fixing portion, the fixed end line, and the free end line uses an N-type impurity as a conductivity-type impurity, a P-type impurity such as boron (B) may be used as the conductivity-type impurity.

In this case, it is desirable that the same type of conductivity-type impurity be used for the beam, the fixing portion, the fixed end line, and the free end line. This application is based on Japanese patent application No. 2008-184837, and the entire disclosure thereof is incorporated herein by reference.

What is claimed is:

1. An impact sensor constructed on a silicon substrate, comprising:
   an insulating layer formed over said silicon substrate;
   a plurality of beams having flexibility that are formed of conductive silicon material;
   a fixing portion to fix a fixed end of each of said beams, said fixing portion being formed of conductive silicon material;
   a fixed end line at whose one end is formed said fixing portion, said fixed end line being formed of conductive silicon material on said insulating layer; and
   a free end line having a pressing portion that faces a free end of each of said beams via a space, said free end line being formed of conductive silicon material on said insulating layer,
   wherein respective beam widths, each measured in a direction orthogonal to a length direction joining said fixed end and said free end, of said plurality of beams are different from each other.

2. The impact sensor according to claim 1, wherein beam widths of the fixed ends of said plurality of beams being the same, beam widths of said beams except said fixed ends are different from each other.

3. The impact sensor according to claim 1, wherein lengths and thicknesses of said plurality of beams are set to be the same.

4. The impact sensor according to claim 2, wherein lengths and thicknesses of said plurality of beams are set to be the same.

5. A method for manufacturing an impact sensor which comprises a plurality of beams having flexibility; a fixing portion to fix a fixed end of each of said beams; a fixed end line at whose one end is formed said fixing portion; and a free end line having a pressing portion that faces a free end of each of said beams via a space, wherein respective beam widths, each measured in a direction orthogonal to a length direction joining said fixed end and said free end, of said plurality of beams are different from each other, said method comprising the steps of:

preparing a silicon substrate;

forming an insulating layer made of silicon nitride over said silicon substrate;

forming said fixed end lines and said free end lines that are made of conductive silicon material on said insulating layer;

forming a sacrifice oxide film made of silicon oxide covering said insulating layer, said fixed end lines, and said free end lines;

flattening the top of said sacrifice oxide film;

forming through holes reaching said fixed end lines in regions of said fixing portions of said fixed end lines, of said flattened sacrifice oxide film;

depositing conductive silicon material into said through holes and onto said sacrifice oxide film by a CVD method to form a conductive silicon layer;

forming a resist mask covering regions where to form said plurality of beams different in beam width on said conductive silicon layer and etching said conductive silicon layer to form said fixing portions and said beams and removing said resist mask; and removing said sacrifice oxide film.

6. The method for manufacturing the impact sensor according to claim 5, comprising the step of dividing said silicon substrate into chips, before said step of removing said sacrifice oxide film when a large number of said impact sensors are formed on said silicon substrate.

7. The method for manufacturing the impact sensor according to claim 5, wherein with said beam widths of the fixed ends of said plurality of beams being the same, the beam widths of said beams except said fixed ends are different from each other.

8. The method for manufacturing the impact sensor according to claim 5, wherein said plurality of beams are formed to have the same length and thickness.

9. The method for manufacturing the impact sensor according to claim 7, wherein said plurality of beams are formed to have the same length and thickness.

* * * * *